US00PP26856P3

(12) United States Plant Patent
Klemm et al.

(10) Patent No.: US PP26,856 P3
(45) Date of Patent: Jun. 21, 2016

(54) ***BEGONIA* PLANT NAMED 'KLEBG14477'**

(50) Latin Name: ***Begonia* sp.**
Varietal Denomination: KLEBG14477

(71) Applicant: Klemm+Sohn GmbH & Co. KG, Stuttgart (DE)

(72) Inventors: Nils Klemm, Stuttgart (DE); Silke Wagener, Leinfelden-Echterdingen (DE)

(73) Assignee: Klemm+Sohn Gmbh & Co. KG, Stuttgart (DE)

( * ) Notice: Subject to any disclaimer, the term of this patent is extended or adjusted under 35 U.S.C. 154(b) by 137 days.

(21) Appl. No.: 14/120,251

(22) Filed: May 13, 2014

(65) Prior Publication Data

US 2015/0334902 P1 Nov. 19, 2015

(51) Int. Cl.
*A01H 5/02* (2006.01)

(52) U.S. Cl.
USPC ..... Plt./343

(58) Field of Classification Search
USPC ..... Plt./343
See application file for complete search history.

*Primary Examiner* — Keith Robinson
(74) *Attorney, Agent, or Firm* — Barbara Campbell; Bethany R. Roahrig; Cochran Freund & Young, LLC

(57) ABSTRACT

A new *Begonia* plant particularly distinguished by a dark red flower color, a compact form, and an upright and mounding plant habit with free branching, is disclosed.

2 Drawing Sheets

Genus and species: *Begonia* sp.
Variety denomination: 'KLEBG14477'.

BACKGROUND OF THE NEW PLANT

The present invention comprises a new and distinct variety of *Begonia*, botanically known as *Begonia* sp., and hereinafter referred to by the variety name 'KLEBG14477'. 'KLEBG14477' originated from a cross-pollination conducted between June to July 2009 in Stuttgart, Germany between the proprietary female *Begonia* variety 'TE 01' (unpatented) and the proprietary male *Begonia* variety 'PL02' (unpatented).

The seeds from the cross were sown and plants were grown in a greenhouse for evaluation, where an individual plant designated 'KLEBG14477' was selected from the group of plants between May to June 2010 in Stuttgart, Germany. In June 2010, 'KLEBG14477' was first vegetatively propagated by vegetative stem tip cuttings. 'KLEBG14477' was found to reproduce true to type in successive generations of asexual propagation in Stuttgart, Germany via vegetative stem tip cuttings.

SUMMARY

The following are the most outstanding and distinguishing characteristics of this new variety when grown under normal horticultural practices in Stuttgart, Germany.

1. Dark-red flower color;
2. A compact form; and
3. An upright and mounding plant habit with free branching.

DESCRIPTION OF THE PHOTOGRAPHS

This new *Begonia* plant is illustrated by the accompanying photographs of the variety grown in a glass greenhouse in Stuttgart, Germany. The colors shown are as true as can be reasonably obtained by conventional photographic procedures.

DESCRIPTION OF THE NEW VARIETY

Figure 1:
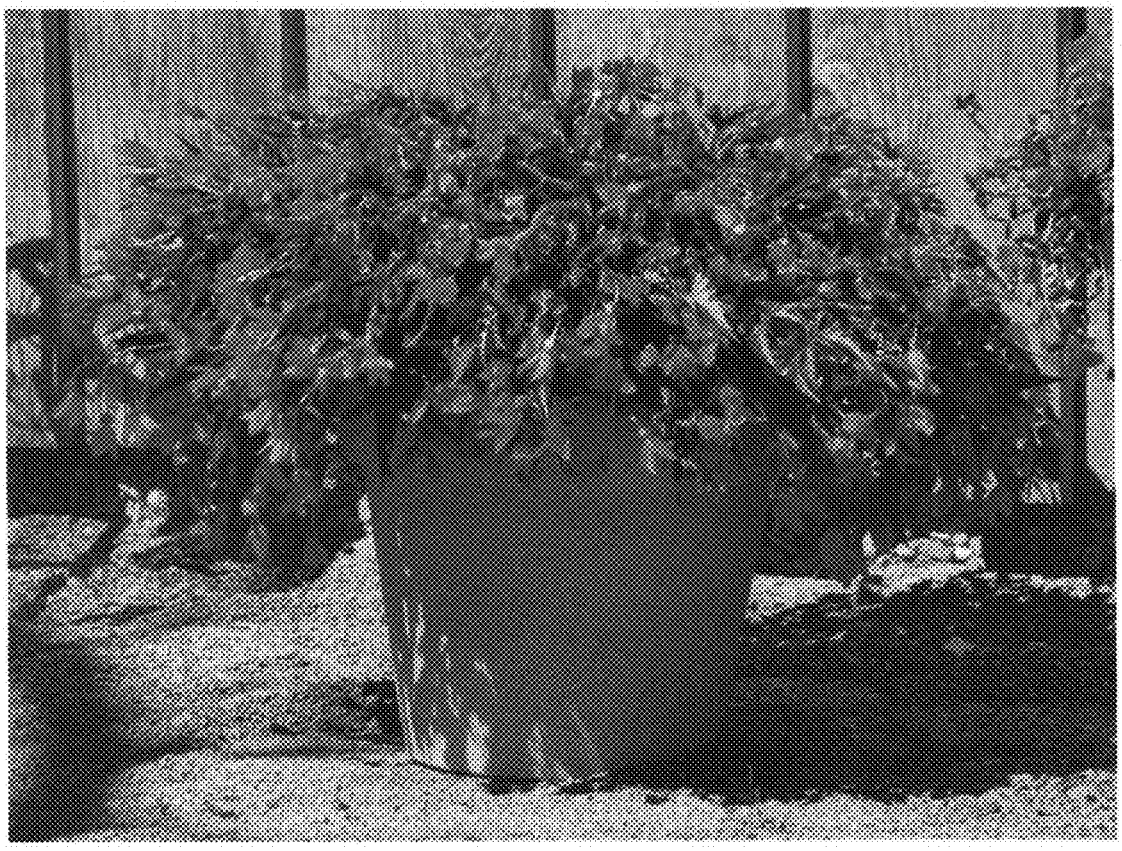
FIG. 1 shows the foliage, habit, and flowers of a 5 to 6-month old plant grown in a pot taken in July 2013.
Figure 2:
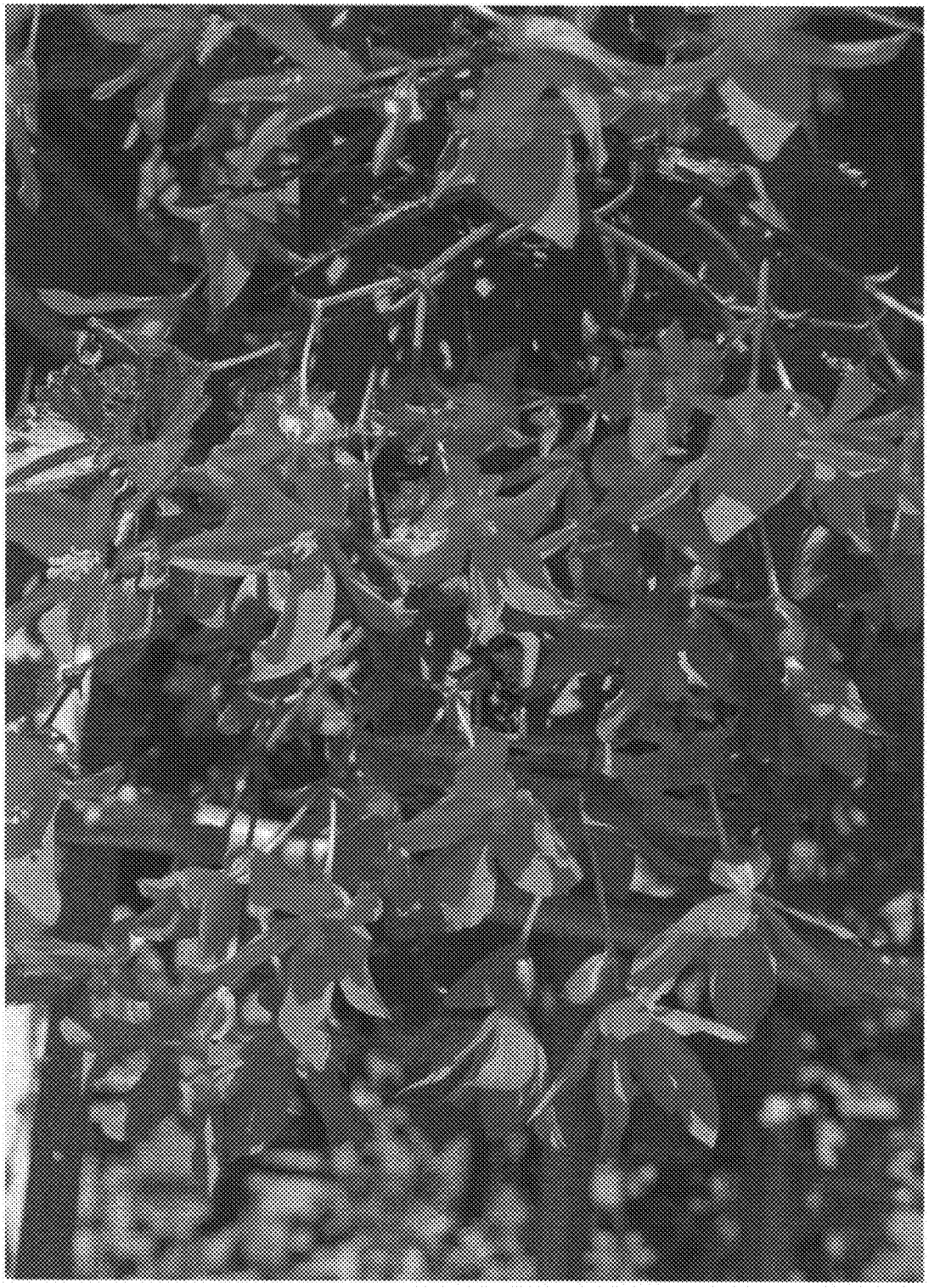
FIG. 2 shows a close-up of the flowers of a 5 to 6-month old plant taken in August 2013.

The following detailed descriptions set forth the distinctive characteristics of 'KLEBG14477'. The data which define these characteristics were collected from asexual reproductions carried out in Stuttgart, Germany. Data was collected on 3-month old plants grown in a greenhouse under natural and artificial light. Color references are to The R.H.S. Colour Chart of The Royal Horticultural Society of London (R.H.S.), $5^{th}$ edition (2007).

Classification:
- *Family*.—Begoniaceae.
- *Botanical*.—*Begonia* sp.
- *Common*.—*Begonia*.
- *Designation*.—'KLEBG14477'.

Parentage:
- *Female parent*.—The proprietary female *Begonia* variety 'TE 01' (unpatented).
- *Male parent*.—The proprietary male *Begonia* variety 'PL02' (unpatented).

Plant:
- *Form*.—Compact.
- *Habit*.—Upright and mounded, free branching.
- *Plant height*.—17.0 cm.
- *Plant width*.—30.0 cm to 35.0 cm.
- *Flower type*.—Single.
- *Time to produce a finished flowering plant*.—2 months.
- *Propagation type*.—Vegetative stem tip cutting.
- *Time to initiate roots*.—About 2 weeks.

*Root description*.—Free-branching, white to brown in color (between RHS 155A and RHS 158A).

Lateral branches:

*Quantity per plant*.—About 6 basal branches.

*Color*.—RHS 184A and RHS N138B.

*Length*.—10.0 cm to 14.0 cm.

*Diameter*.—0.5 cm to 1.0 cm.

*Internode length*.—About 2.0 cm to 4.0 cm.

*Texture*.—Smooth.

*Anthocyanin*.—Some anthocyanin, RHS 176C, mainly on the younger branches.

Foliage:

*Arrangement*.—Alternate.

*Length*.—About 10.0 cm.

*Width*.—About 4.0 cm to 5.0 cm.

*Shape*.—Lanceolate, strongly asymmetric with one side ovate.

*Apex*.—Acuminate.

*Base*.—Oblique, cordate.

*Margin*.—Serrate with short bristles emerging from the tips of the teeth.

*Texture*.—Upper surface: Smooth in the center; towards the margin, sparsely covered with hairs. Lower surface: Sparsely covered with hairs.

*Immature leaf color*.—Upper surface: RHS 43A. Lower surface: RHS 148B.

*Mature leaf color*.—Upper surface: RHS 136B. Lower surface: RHS 139C.

*Venation pattern*.—Pinnate and palmate.

*Venation color*.—Upper surface: RHS 143D. Lower surface: RHS 139C with some anthocyanin, mainly in the basal area.

*Petioles*.—Length: 1.5 cm to 2.5 cm. Diameter: 0.2 cm. Color: RHS 176B. Texture: Pubescent, a covering of fine, colorless hairs.

Flowers:

*Inflorescence type*.—Single flowers arranged in axillary cymes.

*Quantity of flowers per cyme*.—1 to 2.

*Quantity of cymes per plant*.—About 15 for a 3-month old plant.

*Flowering season*.—Spring to autumn.

*Lastingness of individual flowers on the plant*.—About 1 to 2 weeks.

*Fragrance*.—Absent.

*Bracts*.—Quantity per flower: 2. Length: About 0.8 cm. Width: About 0.1 cm. Shape: Round. Apex: Obtuse. Base: Rotundate. Margin: Medium. Color: Upper surface: RHS 45D. Lower surface: RHS 45C.

*Peduncle*.—Length: 5.0 cm. Diameter: 0.2 cm. Color: RHS 179C. Texture: Smooth.

*Female flowers*.—Bud: Shape: Flattened ovate. Height: About 2.0 to 2.5 cm. Width: About 1.5 cm. Color: RHS 46A. Texture: Smooth. Flowers: Shape: Single radian bell-mouthed. Depth/height: 4.0 cm. Width: 5.0 cm. Tepals: Quantity per flower: 5 total; 3 outer and 2 inner. Inner tepals: Shape: Reverse lanceolate. Length: 4.2 cm. Width: 1.3 cm. Color (both upper and lower surfaces): RHS 45A and RHS 45B. Texture: Smooth. Outer tepals: Shape: Elliptic, obtuse base, acute to obtuse apex. Length: 3.8 cm. Width: 1.6 cm. Color (both upper and lower surfaces): RHS 45A and RHS 45B. Texture: Smooth. Pedicels: Length: About 3.5 cm. Diameter: About 0.1 cm. Color: RHS 151D and a little RHS 44D. Texture: Smooth.

*Male flowers*.—Flower type: Single. Shape: Bilateral bell-mouthed. Depth/height: 4.0 cm. Width: 6.0 cm. Tepals: Quantity per flower: 4 total; 2 outer and 2 inner. Inner tepals: Shape: Reverse lanceolate. Length: 4.8 cm. Width: About 1.5 cm. Color (both upper and lower surfaces): RHS 45A and RHS 45B. Texture: Smooth. Outer tepals: Shape: Ovate, rotundate base, obtuse apex. Length: About 4.2 cm. Width: About 2.5 cm. Color (both upper and lower surfaces): RHS 45A and RHS 45B. Texture: Smooth. Pedicel: Length: About 2.0 cm. Diameter: About 0.1 cm. Color: RHS 44D. Texture: Smooth.

Reproductive organs:

*Stamens* (*on the male flowers*).—Quantity per male flower: About 35. Anther shape: Lanceolate. Anther length: 0.15 cm. Anther color: RHS 17A. Pollen amount: Moderate. Pollen color: RHS 8C.

*Pistils* (*on the female flowers*).—Quantity per female flower: 3. Pistil length: About 1.8 cm. Style length: 0.8 cm including extension. Style color: RHS 45B. Stigma shape: Bifid, twisted around extension of the style. Stigma color: RHS 17A. Ovary color: RHS 145A, and the tips are RHS 42B.

Fruit and seed set: No fruit and seed set observed.

Disease and pest/insect resistance: No disease and pest/insect resistance observed.

COMPARISON WITH PARENTAL LINES AND KNOWN VARIETY

'KLEBG14477' is a distinct variety of *Begonia* and is distinguished from its parents as described in Table 1.

TABLE 1

Comparison with Parental Lines

| Characteristic | 'KLEBG14477' | Female Parent 'TE 01' | Male Parent 'PL02' |
|---|---|---|---|
| Flower color | Dark red | Red | Light pink |

'KLEBG14477' is a distinct variety of *Begonia* and is most similar to the commercial *Begonia* variety 'KLEBG13465' (U.S. Plant patent application Ser. No. 14/120,250). Differences between the varieties are described in Table 2.

TABLE 2

Comparison with Similar Variety

| Characteristic | 'KLEBG14477' | 'KLEBG13465' |
|---|---|---|
| Flower color | Dark red | Orange-red |

We claim:

1. A new and distinct variety of *Begonia* plant designated 'KLEBG14477' as illustrated and described herein.

* * * * *